(12) United States Patent
Farr et al.

(10) Patent No.: US 6,450,969 B1
(45) Date of Patent: Sep. 17, 2002

(54) DEVICE FOR MEASURING INSPIRATORY STRENGTH

(75) Inventors: Philip William Farr, Ware; Thomas Paul McCarthy, Uxbridge, both of (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/622,514

(22) PCT Filed: Feb. 15, 1999

(86) PCT No.: PCT/EP99/00949
§ 371 (c)(1),
(2), (4) Date: Jan. 5, 2001

(87) PCT Pub. No.: WO99/42033
PCT Pub. Date: Aug. 26, 1999

(30) Foreign Application Priority Data

Feb. 17, 1998 (GB) ............................................. 9803363
Jul. 30, 1998 (GB) ............................................. 9816677

(51) Int. Cl.$^7$ ................................................. A61B 5/08
(52) U.S. Cl. .................. 600/538; 600/529; 600/533
(58) Field of Search .................. 600/538, 540, 600/533, 529

(56) References Cited

U.S. PATENT DOCUMENTS

| | | | | |
|---|---|---|---|---|
| 3,635,214 A | * | 1/1972 | Rand | 600/540 |
| 3,924,611 A | | 12/1975 | Galitsky | |
| 4,171,804 A | * | 10/1979 | Thead, Jr. | 482/13 |
| 4,350,167 A | * | 9/1982 | Heimlich | 600/540 |
| 4,425,923 A | * | 1/1984 | Gordon et al. | 600/540 |
| 4,499,905 A | * | 2/1985 | Greenberg et al. | 600/540 |
| 4,533,137 A | * | 8/1985 | Sonne | 482/13 |
| 4,693,256 A | * | 9/1987 | Talonn | 600/538 |
| 4,768,520 A | * | 9/1988 | Varraux et al. | 600/538 |
| 5,547,440 A | * | 8/1996 | Rubens et al. | 482/13 |
| 5,984,873 A | * | 11/1999 | Crumb et al. | 600/538 |
| 6,083,141 A | * | 7/2000 | Hougen | 482/13 |

FOREIGN PATENT DOCUMENTS

WO    WO 96 37147 A    11/1996

* cited by examiner

Primary Examiner—Kevin Shaver
Assistant Examiner—Patricia Mallari
(74) Attorney, Agent, or Firm—Christopher P. Rogers

(57) ABSTRACT

A device having variable inspiratory resistance suitable for measuring the inspiratory strength of a patient which comprises a chamber in communication with a mouthpiece. The chamber is provided with a calibration system for measuring the inhalation flow rate during inhalation through the mouthpiece. The calibration system is also provided with a variable resistance feature where the airflow resistance may be altered.

21 Claims, 5 Drawing Sheets

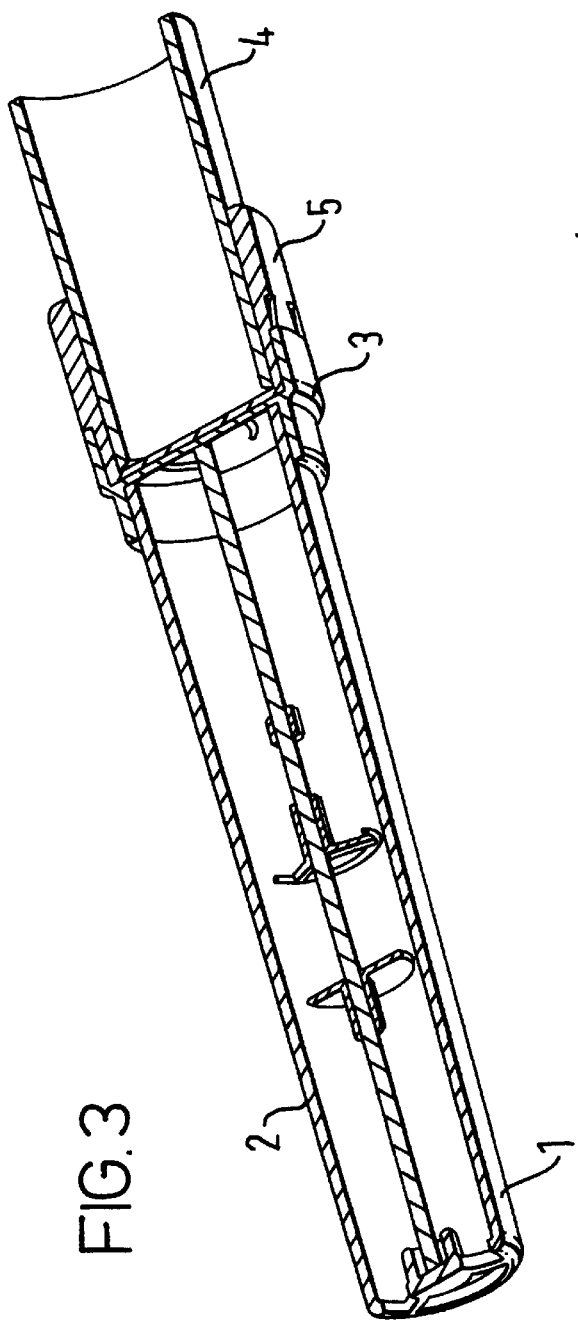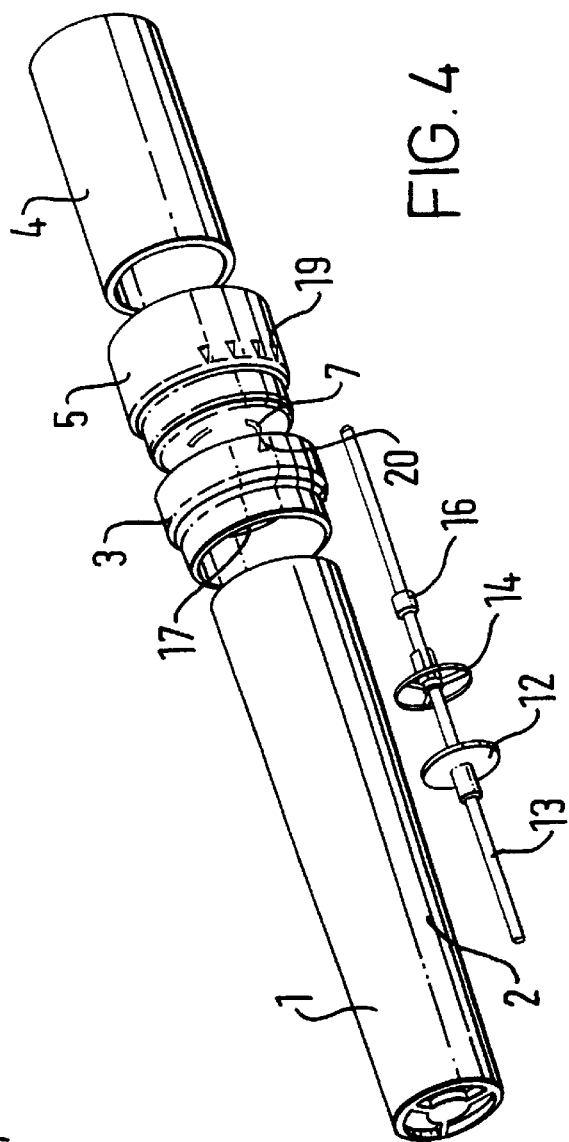

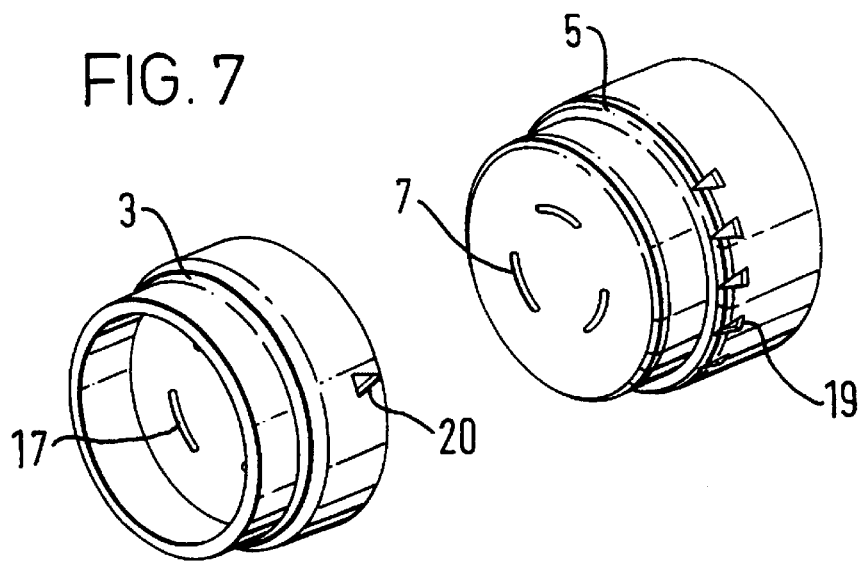
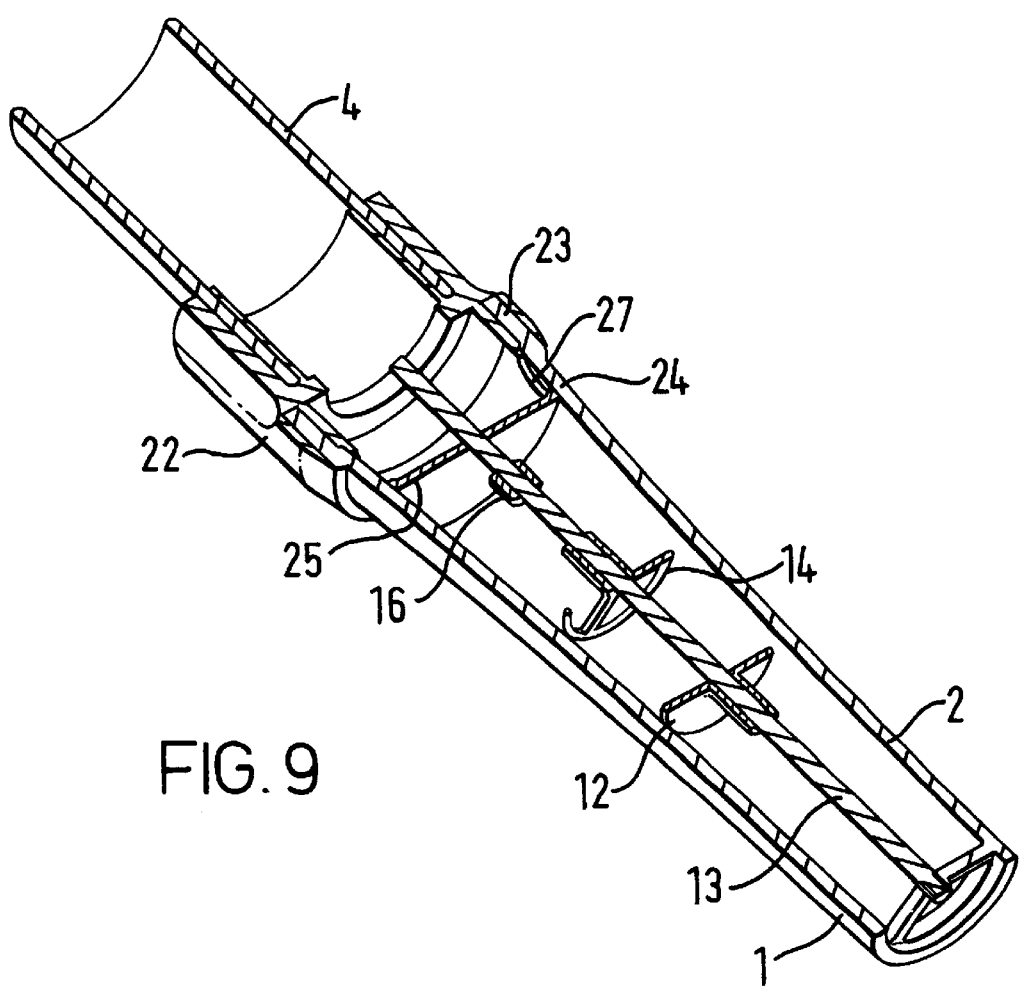

DEVICE FOR MEASURING INSPIRATORY STRENGTH

This application is filed pursuant to 35 U.S.C. §371 as a United States National Phase Application of International Application No. PCT/EP99/00949, which claims priority from GB9803363.2 filed Feb. 17, 1998 and GB9816677.0 filed Jul. 30, 1998.

This invention relates to an inhalation device suitable for measuring the inspiratory strength of a patient and a method of using the same.

A number of inspiratory flow meters are known which may be used to measure inspiration flow rate, and length of inspiration achieved by a patient.

U.S. Pat. No. 5,167,506 describes an inhalation device training system which comprises a sensor which continuously measures the inhalation flow rate during inhalation through the mouthpiece and provides an electric signal which varies continuously with flow rate. The electrical signal is useful for monitoring inspiration flow rate, and length of inspiration, amongst other parameters.

Inhalation devices are known to be used for local administration of drugs to the respiratory tract and lungs of patients suffering from respiratory disorders e.g. asthma. Medicament for administration by inhalation should be of a controlled particle size in order to achieve maximum penetration into the lungs, preferably in the range of 1 to 10 micrometers in diameter and more preferably 1 to 5 micrometers. Unfortunately, powders in this particle size range, for example micronised powders, usually have very poor flow characteristics due to the cohesive forces between the individual particles which make them readily agglomerate together to form bridges which are not readily broken apart to become free flowing. These agglomerates of powder can be easily handled and may be used to fill powder inhalation devices. However, for efficient delivery to the lungs, the powder agglomerates must be broken down before they leave the device, back into a controlled size. It has been found that it is possible to break up powder agglomerates in the airflow as a user inhales by incorporating a series of baffles in the mouthpiece of a powder inhalation device. The baffles create turbulence and cause the air flow to collide with the baffles promoting the disintegration of powder agglomerates entrained in the air flow to render the powder in a form suitable for inhalation therapy. The use of these baffles in such devices creates a resistance to airflow within the device. Examples of such devices are Rotohaler™, Diskhaler™ and Turbohaler™.

Different metered dose inhalers have different levels of resistance associated with them, because of the varying device designs. Persson's study (Eur Respir J. 1997 10 681–684) has shown that the inhalation effort required to use inhalation devices effectively depends in the peak inspiratory flow achievable by the subjects. It is also acknowledged in this study that a minimum flow rate is needed to achieve efficient use of inhalation devices, and this flow rate can differ with type of device.

However, the problem with the inspiratory flow rate meters known is that whilst they measure the maximum inspiratory flow rate achievable by a patient under little or no resistance, they do not indicate the effort expended by a patient to achieve such a rate. The maximum flow rate achievable by a patient is affected by the resistance to airflow associated with a meter. In the context of inhalation therapy, more severely affected patients may not have the inspiratory strength to be able to achieve flow rates above a certain minimum, if the resistance of the meter is too great. This is important as the effectiveness for a given inhalation device is dependent on patient's flow rate being above a certain minimum level, such levels differing between devices. It is therefore crucial to the selection of appropriate therapeutic treatment to be able to measure the inspiratory strength of a patient.

According to the invention there is provided a device having inspiratory resistance suitable for measuring the inspiratory strength of a patient which comprises a chamber in communication with a mouthpiece, said chamber being provided with a calibrated system for measuring the inhalation flow rate during inhalation through the mouthpiece and said chamber having a system by which the resistance to airflow through the device can be altered.

A device according to the invention is simple to use and provides clinicians with a useful tool with which to teach patients how to use various inhalation devices efficiently by allowing a patient to experience how to achieve the desired flow rate under the correct resistance. It also allows clinicians to select the most suitable inhalation device for a patient, taking into account the patient's ability to produce the minimum airflow rate needed to operate the device efficiently.

Preferably the device comprises an elongate chamber defining a through-going pathway having first and second ends; wherein the calibration system comprises a sliding member which is retained within the chamber between the first and second ends and slides within the chamber when the pressure at the first end of the chamber is reduced by patient inspiration and where the variable resistance feature comprises means for varying the area through which the air enters the second end of the chamber such that the inspiratory resistance of the device may be varied by altering the area through which the air enters the chamber at the second end of the chamber.

Alternately and more preferably the device comprises an elongate chamber defining a through-going pathway having first and second ends; wherein the calibration system comprises a sliding member which is retained within the chamber between the first and second ends and slides within the chamber when the pressure at the first end of the chamber is reduced by patient inspiration and where the variable resistance feature comprises means for varying the area through which the air leaves the first end of the chamber to the mouthpiece such that the inspiratory resistance of the device may be varied by altering the area through which the air leaves the chamber at the first end of the chamber.

The chamber may at its first end incorporate a cap located between the first end of the chamber and the mouthpiece to reduce the area of the chamber.

Preferably the chamber is of circular cross section and more preferably tapered so that the cross section at the mouthpiece end is greater than at the second end.

Preferably the calibration system comprises calibrations along the length of the chamber such that the distance of travel of the sliding member along the chamber from its resting position during patient inspiration is indicative of the maximum inspiratory flow rate of the patient. In this embodiment the chamber will be transparent or translucent to enable the position of the sliding member to be seen.

Alternatively the calibration system comprises calibrations along the length of the sliding member such that the distance of travel of the sliding member along the chamber from its resting position during patient inspiration is indicative of the maximum inspiratory flow rate of the patient.

Preferably the sliding member is provided with means to guide its movement along the length of the chamber.

Even more preferably the guiding means comprise a rod located along the axis of the chamber along which the sliding member moves on patient inspiration.

Preferably a means for enabling the sliding member to be restored to its resting position after use is provided.

Even more preferably the means for enabling the sliding member to be restored to its resting position after use comprises a weight.

Preferably the means for varying the area through which the air enters the second end of the chamber or leaves the first end of the chamber comprises an iris, and even more preferably the iris has two or more defined aperture size settings.

Alternatively and more preferably the means for varying the area through which the air enters the second end of the chamber or leaves the first end of the chamber comprises the provision of two co-operating aperture bearing plates, such that by choice of relative orientation of the two plates the size of the area through which air enters the second end of the chamber or leaves the first end of the chamber, may be varied.

Preferably each plate is provided with at least two apertures.

Preferably two or more specified orientations of the two co-operating aperture-bearing plates are provided to define two or more specified areas through which air enters the device.

Even more preferably at least one specified orientation of the two co-operating aperture-bearing plates provides the device with a resistance matching that of an inhalation device.

In an alternative embodiment the area through which the air enters the second end of the chamber or leaves the first end of the chamber is defined by a ring formed between the inner surface of a portion of the chamber and the outer surface of a portion of a co-operating section having one or more apertures, at least one of the chamber and the co-operating section being tapered in said portion, whereby movement of the chamber relative to the co-operating section, along the longitudinal axis of the chamber alters the area of the ring, and hence the resistance to air flow. On inhalation by the patient, air may flow through the device, via the apertures and the ring.

Preferably the co-operating section is situated between the first end of the chamber and the mouthpiece.

Preferably the outer surface of the portion of the co-operating section is tapered.

It is particularly preferred that the taper is a curved taper.

More preferably both the inner surface of the portion of the chamber and the outer surface of the portion of the co-operating section are tapered.

Most preferably both tapers are curved tapers.

Preferably the curve of the taper will be configured to give resolution of the calibration scale.

Preferably the movement is rotational movement of the co-operating section relative to the chamber which leads to transitional movement of the co-operating section relative to the chamber along the longitudinal axis of the chamber. This facilitates calibration.

Preferably the co-operation between the chamber and co-operating section is by means of a screw and thread system.

Preferably two or more specified positions along the longitudinal axis of the device are provided to define two or more areas of the ring. Preferably these positions are defined by lining up a mark on the co-operating section with a mark on the chamber.

Even more preferably at least one specified position along the longitudinal axis provides the device with a resistance matching that of an inhalation device.

Preferably the co-operating section has at least two apertures.

Preferably the apertures are arranged symmetrically around the co-operating section.

A further aspect of the invention is a method of measuring the inspiratory strength of a patient by use of a device according to any preceding claim which comprises measuring the effort required to obtain a inspiratory flow rate as measured by the calibration system, at different resistance settings of the variable resistance feature.

Even more preferably this method comprises measuring the effort required to move the sliding member a desired distance along the chamber at different settings of the area through which the air enters the chamber at the second end of the chamber or leaves the first end of the chamber.

Another aspect of the invention is a device adapted for use with any conventional inspiratory flow rate meter which comprises a variable resistance feature providing means for varying the resistance to airflow through the inspiratory flow rate meter.

The invention is further described below with reference to the accompanying drawings in which:

FIG. 3 is a cross section through an alternative embodiment of the invention;

FIG. 4 is an exploded perspective view of the device of FIG. 3;

FIG. 7 is an exploded perspective view of the variable resistance means as used in the device of FIGS. 5 and 6.

FIG. 9 is a cross-section of the device of FIG. 8 in a closed position so that there is no air flow through the device.

Figure 1:
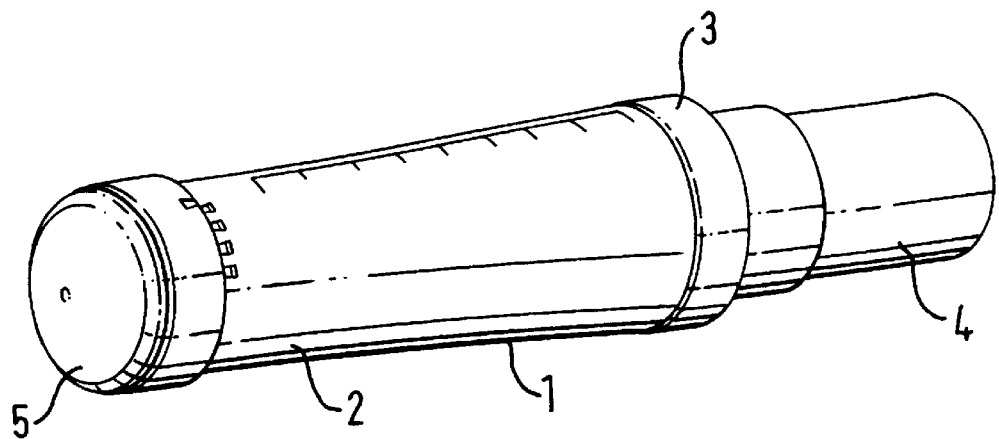
FIG. 1 is a perspective view of the assembled device according to the invention.
Figure 2:
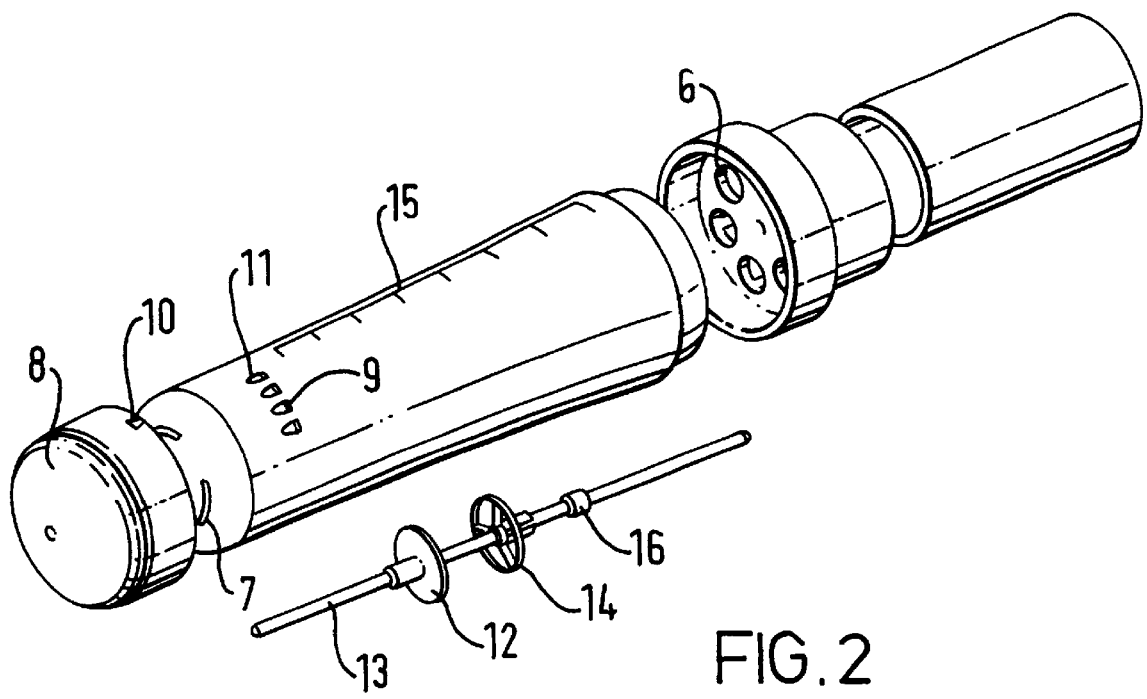
FIG. 2 is an exploded perspective view of the device of FIG. 1 showing the main body components.

In the embodiment of FIG. 1, the device comprises a body 1 formed of a chamber 2 and cap 3 both of which may be moulded from a plastics material such as polycarbonate and a disposable mouthpiece section 4 through which a user can inhale which may advantageously made of cardboard. The variable resistance feature 5 is rotationally connected to the chamber 2. As seen in FIG. 2, the cap 3 is provided with apertures 6 to allow airflow from the chamber through the mouthpiece 4 on inhalation by a user. The chamber 2 is provided with slots 7 and the variable resistance means is provided with holes 8. Different relative orientations of the variable resistance feature 5 and the chamber 2 result in different quantities of overlap between the slots 7 and the holes 8, resulting in different resistances to airflow on inhalation by the user. The different resistances are indicated on the resistance calibration scale 9 when the mark 10 on the variable resistance feature 5 is aligned with different marks 11 on the chamber 2. The sliding member 12 is movably mounted on the guide rod 13 which is retained within the chamber 2. On inhalation by the user, the sliding member 12 and indicator 14 are drawn by the airflow along the guide rod 13. The indicator 14 comes to rest when the maximum flow rate is achieved and this rate can be measured by the position of the indicator 14 against the calibrated flow rate scale 15.

The maximum flow rate is dependent on the level of resistance to airflow indicted by the resistance calibration scale 9. In general a resistance calibration scale is provided for each resistance feature. The indicator 14 is returned to its resting position after use by the weight 16.

FIGS. 3, 4, 5, 6 and 7 show an alternative embodiment where the variable resistance feature 5 is situated between the cap 3 and the mouthpiece 4. The different levels of resistance are achieved by aligning the slots 7 in the variable resistance feature 5 with the slots 17 in the cap 3. The different resistances are indicated on the resistance calibration scale 9 when one of the marks 19 on the variable resistance feature 5 is aligned with mark 20 on the cap 3.

Figure 5:
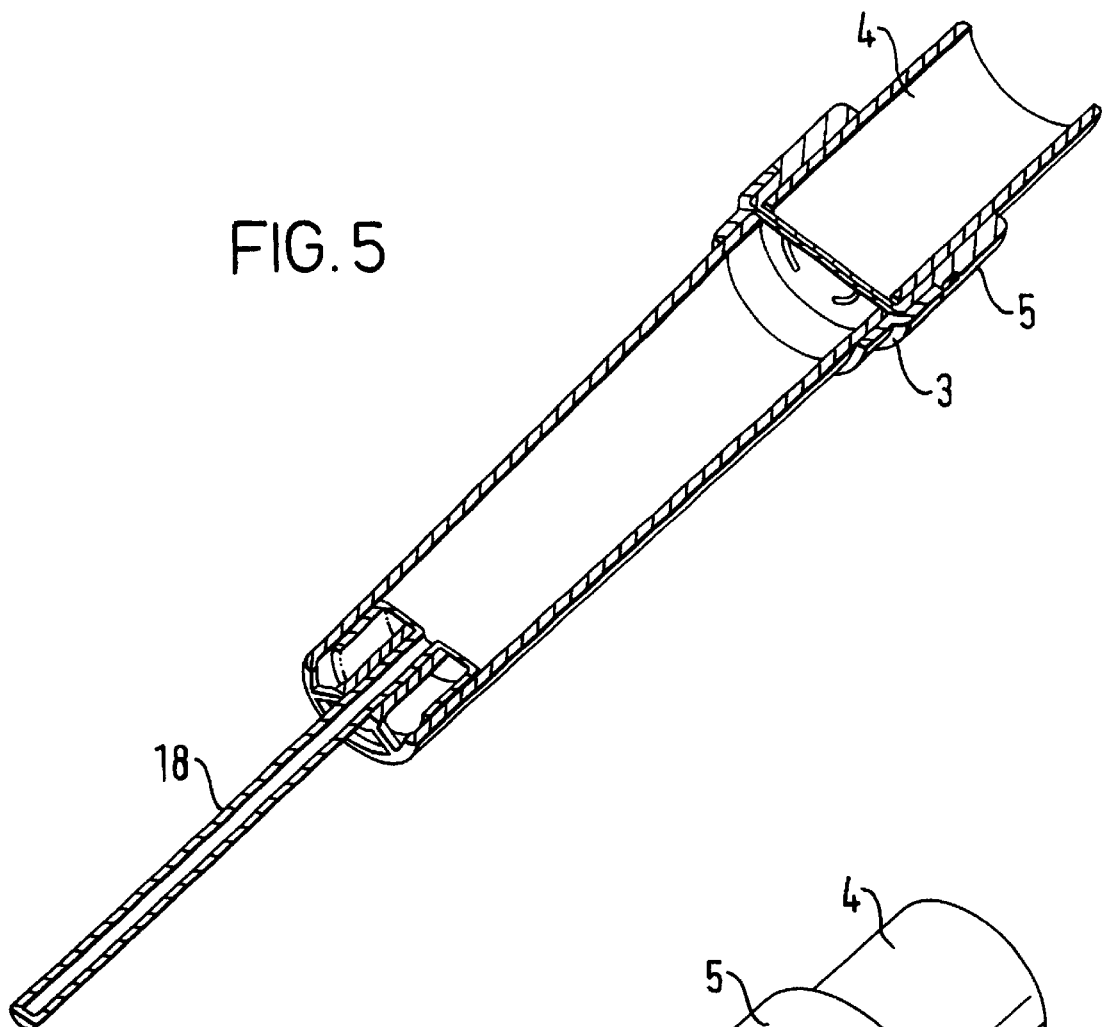
FIG. 5 is a cross section through an alternative embodiment of the invention.
Figure 6:
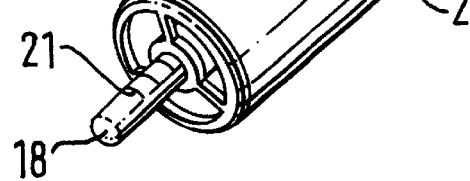
FIG. 6 is a perspective view of the device of FIG. 5.

An alternative sliding means is shown in FIGS. 5 and 6 where inhalation by the user through the mouthpiece 4 causes the plunger 18 to be drawn into the chamber 2 and the maximum flow rate is indicted by position of the plunger 18 with respect to the chamber 2 on the calibrated scale 21 on the plunger 18.

Figure 8:
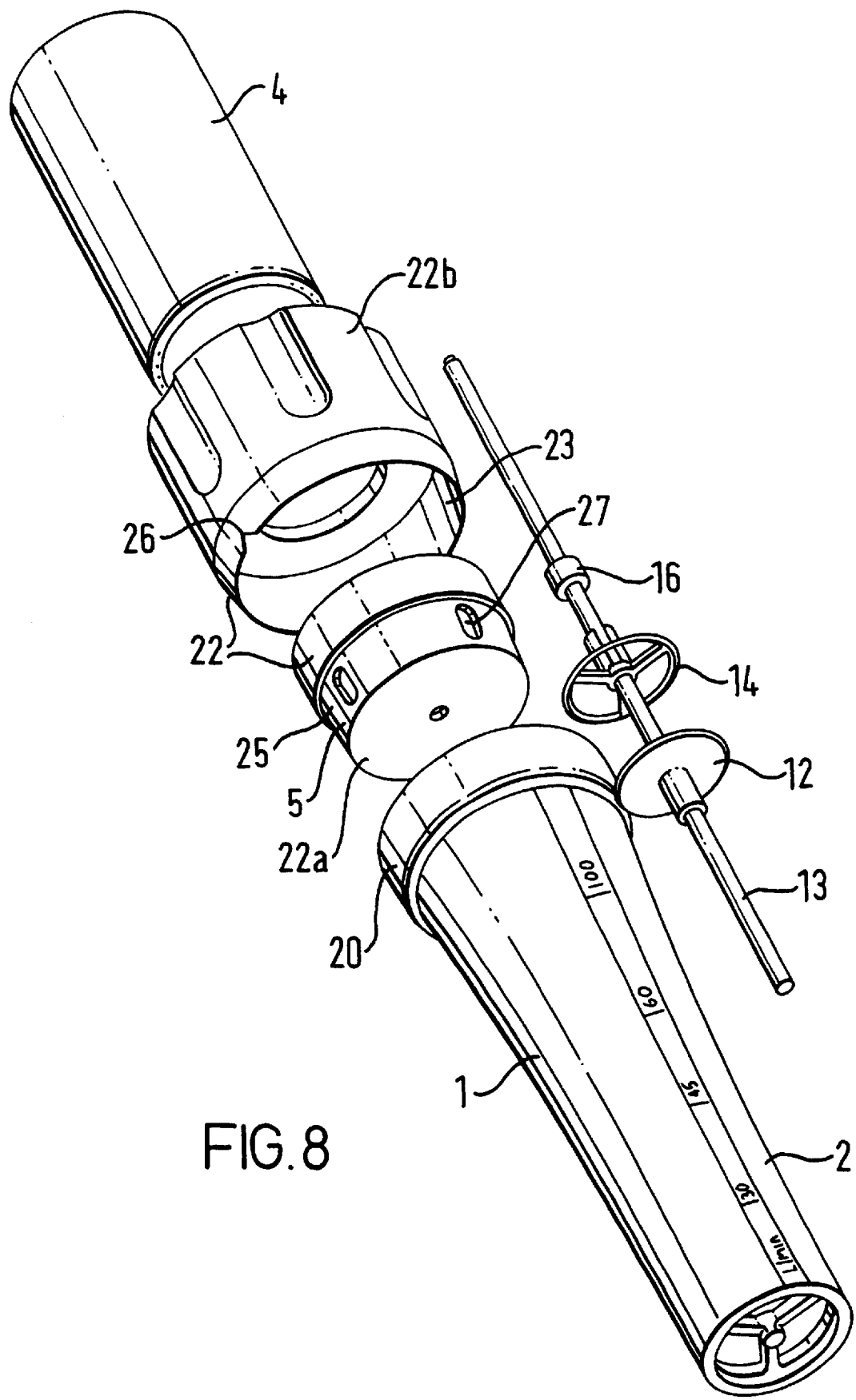
FIG. 8 is an exploded perspective view of an alternative embodiment of the invention.

FIGS. 8 and 9 show an alternative embodiment where the variable resistance feature 5 is situated between the chamber 2 and the mouthpiece 4. Rotational movement of the co-operating section 22 (shown here as two independent components, 22a and 22b) connected by a screw and thread system 23 to chamber 2 causes movement of the co-operating section 22 relative to the chamber 2 along the longitudinal axis of the device, so increasing and decreasing area of the ring defined by the distance between the inner surface 24 of the chamber and the outer surface 25 of the co-operating section 22 providing different levels of resistance.

Whilst the co-operating section can be advantageous manufactured in two parts, which parts are then fixed permanently together on assembly, as illustrated, it will be appreciated that it may alternatively be manufacture in a single part.

The level of resistance is indicated on the resistance calibration scale when the notch 26 is aligned with a mark 20 on the chamber 2.

On inhalation by the user, air flows through the device by way of the chamber 2, through the ring formed between the inner surface 24 of the chamber and the outer surface 25 of the co-operating section 22 through the apertures 27 into the co-operating section and then leaves the device via the mouthpiece 4.

What is claimed is:

1. A device having variable inspiratory resistance suitable for measuring the inspiratory strength of a patient comprising:
    an elongate chamber having, first and second ends, in communication with a mouthpiece including: a calibration system adapted to measure the inhalation flow rate and a variable resistance system adapted to vary the resistance to airflow through the device;
    wherein the airflow area of the first end of the chamber is defined by the inner surface of a portion of the chamber and by the outer surface of a portion of a plurality of co-operating plates each having one or more apertures;
    wherein a portion of at least one of the chambers and co-operating plates are at least partially tapered;
    wherein the co-operating plates are situated between the first end of the chamber and the mouthpiece;
    wherein the outer surface of the co-operating plate is tapered, and
    wherein the calibration system comprises a sliding member adapted to be retained within the chamber when the pressure at the first end of the chamber is reduced by patient inspiration.

2. A device as claimed in claim 1 wherein the chamber is of circular cross sectional area.

3. A device as claimed in claim 2 wherein the calibration system comprises calibrations along the length of the chamber, wherein the distance traveled by a sliding member along the chamber from a resting position during patient inspiration is indicative of the maximum inspiratory flow rate of the patient.

4. A device claimed in claim 1 wherein the sliding member is provided with a guide.

5. A device as claimed in claim 4 wherein the guide includes a rod located along the axis of the chamber along which the sliding member moves upon patient inspiration.

6. A device as claimed in claim 5 further comprising a weight adapted to restore the sliding member to the resting position after use.

7. A method of measuring the inspiratory strength of a patient by use of the device according to claim 1 comprising:
    providing the device of claim 1, and measuring the effort required to obtain an inspiratory flow rate with the calibration system.

8. A method of measuring the inspiratory strength of a patient by use of the device of claim 1 comprising:
    providing the device of claim 1, and measuring the effort required to move the sliding member a suitable distance along the chamber.

9. A device as claimed in claim 1 wherein the variable resistance system is an iris.

10. A device as claimed in claim 9 wherein the iris has two or more defined aperture size settings.

11. A device as claimed in claim 1 wherein the variable resistance system includes two co-operating aperture bearing plates adapted to be variously oriented.

12. A device as claimed in claim 11 wherein each plate is provided with at least two apertures.

13. A device as claimed in claim 12 wherein two or more orientations of the two co-operating aperture bearing plates define two or more specified areas through which air enters the device.

14. A device as claimed in claim 13 wherein at least one orientation of the two co-operating aperture-bearing plates is adapted to provide a resistance suitable for inhalation.

15. A device as claimed in claim 1 wherein the inner and outer surface of the plates are tapered.

16. A device as claimed in claim 15 wherein the plates are adapted to rotate and to transition along the longitudinal axis of the chamber.

17. A device as claimed in claim 16 further including a screw and thread system.

18. A device as claimed in claim 1 wherein two or more specified positions along the longitudinal axis of the device are provided to define two or more areas of the ring.

19. A device as claimed in claim 18 wherein at least one position along the longitudinal axis provides the device with a resistance suitable for inhalation.

20. A device as claimed in claim 19 wherein at least one plate has at least two apertures.

21. A device as claimed in claim 20 wherein the apertures are arranged symmetrically around a co-operating section.

* * * * *